United States Patent [19]

Werges

[11] 4,067,902

[45] * Jan. 10, 1978

[54] MIXING TWO IMMISCIBLE FLUIDS OF DIFFERING DENSITY

[75] Inventor: Darrell L. Werges, Park Forest, Ill.

[73] Assignee: Nalco Chemical Company, Chicago, Ill.

[*] Notice: The portion of the term of this patent subsequent to Aug. 26, 1992, has been disclaimed.

[21] Appl. No.: 574,379

[22] Filed: May 5, 1974

Related U.S. Application Data

[62] Division of Ser. No. 428,064, Dec. 26, 1973, Pat. No. 3,929,421.

[51] Int. Cl.$^2$ .......................................... C07C 103/08
[52] U.S. Cl. ................................ 260/561 N; 260/641
[58] Field of Search .................................... 260/561 N

[56] References Cited

U.S. PATENT DOCUMENTS

| | | | |
|---|---|---|---|
| 3,696,152 | 10/1972 | Habermann et al. | 260/561 R |
| 3,766,088 | 10/1973 | Yoshimura et al. | 260/561 N |
| 3,767,706 | 10/1972 | Habermann et al. | 260/561 N |
| 3,894,084 | 7/1975 | Werges | 260/561 N |
| 3,900,516 | 8/1975 | Werges | 260/561 N |
| 3,901,943 | 8/1975 | Werges | 260/561 N |

*Primary Examiner*—Helen M. S. Sneed
*Attorney, Agent, or Firm*—Hill, Gross, Simpson, Van Santen, Steadman, Chiara & Simpson

[57] ABSTRACT

Apparatus and method for first mixing continuously at a prechosen flow rate a less dense fluid with a more dense fluid, the fluids being at least partially immiscible, so as to achieve a constant weight ratio of one fluid to the other per prechosen unit of mixed fluid volume transversely across the path of such mixed fluid followed by charging the resulting mixed fluid simultaneously to a multiplicity of tubes in a tubular reactor under conditions of substantially plug flow. At least one of the fluid is a liquid at all times.

13 Claims, 16 Drawing Figures

Fig. 16

MIXING TWO IMMISCIBLE FLUIDS OF DIFFERING DENSITY

This is a division, of application Ser. No. 428,064, filed Dec. 26, 1973, now U.S. Pat. No. 3,929,421.

BACKGROUND OF THE INVENTION

Certain chemical processes involve the interaction of two liquids or fluids of different densities and limited mutual solubility. When these liquids are mixed to form a two-phase system and are then catalytically reacted under strongly exothermic or endothermic conditions, it becomes desirable and even necessary to achieve an intermixing between the two liquids before they are subjected to reaction conditions. With liquids of differing density, it is particularly difficult to achieve a distribution of one liquid in the other, or vice versa, on a uniform basis, even transitorily, because of the inherent physical tendency of such liquids to assume different flow rates, even with all other variables being substantially constant.

For example, the hydration of acrylonitrile to acrylamide is a highly exothermic reaction. The problem of controlling reaction temperature is particularly, and perhaps even uniquely, difficult when using a reactor feed of relatively high acrylonitrile concentration due to the relatively low system heat capacity per mole of reactant acrylonitrile. This results in the necessity of conducting the reaction between acrylonitrile and water when using a concentrated acrylonitrile feed in a reaction zone from which the heat of reaction can be continuously removed to avoid undesirably high temperatures where side reactions may occur.

As those skilled in the art will appreciate, if the heat of reaction is continuously removed from a fixed-bed catalytic reaction zone, the zone or zonal elements must have a relatively small cross-sectional area with a coolant circulated around the outside of the zone or zonal elements. If large cross sectional areas are used for the zone or zonal elements, some areas of the reaction zone are too far from the cooling surface and hence tend to experience undesirably large temperatures. In addition, a small cross sectional area tends to maximize the interfacial area between the reaction zone and the cooling media, which allows removing the heat of reaction efficiently with a relatively small temperature difference between reaction zone and cooling media. In common, normal practice using a tubular reaction zone with a fixed catalytic bed in the zones, it is common to employ tubes having inside diameters in the range of from about 0.4 to 2.6 inches with a circular cross section.

In the case of acrylamide production by a hydrolysis of acrylonitrile, one employs a reaction having a sufficiently large catalyst bed volume to produce commercial quantities of acrylamide at commercial rates. The particular reactor design used can be one which has a multiplicity of longitudinally parallel, transversely spaced tubes positioned within a common shell through which a coolant is circulatable. A single tube is not used because the bed length would be impractically long for a commercial reactor.

In such a reactor or reactors, the feed composition used in making a concentrated acrylamide solution directly is inherently two phased because of the limited solubility of acrylonitrile in water. In a commercial size reaction having a multiplicity of parallel tubes, it is critically important that all tubes receive approximately the same total flow rate per tube of each of the two phases. Thus, if a substantial deviation occurs from this desired equal distribution, the reactor conversion performance will be inherently reduced. In the extreme case, where essentially all water goes through one set of tubes, while substantially all acrylonitrile goes through another set of tubes, conversion is essentially zero.

The achievement of such a mixture having substantially uniform distribution of water and acrylonitrile in two phases at the entrance to each of a multiplicity of reactor tubes presents a formidable problem which does not appear to be solvable by any known technique.

BRIEF SUMMARY OF THE INVENTION

The present invention provides apparatus and method adapted for continuously and simultaneously mixing and then catalytically reacting under strongly exothermic or endothermic conditions two at least partially immiscible fluids of differing density with such two fluids being substantially equally distributed across the entrances of each of a plurality of tubular reaction zones. The respective fluids are separately charged to a distribution zone, suitably intermixed, and fed through the tubular reaction zones. At least one of the fluids is a liquid, and preferably both are liquid and the process conditions employed are preferably always liquid phase.

It is an object of the present invention to provide in a feed distribution zone a technique for obtaining substantially equal distribution between two at least partially immiscible fluids or liquids of differing density under liquid phase conditions in a flow of such liquids to the tubular elements of a tubular reaction zone comprising a plurality of such elements.

It is another object to provide a technique of the type indicated which is particularly well suited for hydrolyzing under liquid phase conditions acrylonitrile to acrylamide using an acrylonitrile rich feed stream of water plus acrylonitrile.

It is another object to provide a technique of the class described which is suitable for use under continuous operating conditions for extended periods of time and which has a minimum of maintenance problems associated with its use.

Another object of this invention is to provide a uniform dispersion of acrylonitrile droplets in a water phase which has a substantially flat velocity profile in the region adjacent to a tubular reaction zone so that the inlet of each tubular zone element is continuously and constantly exposed to a feed mixture of approximately uniform composition.

Another object is to provide a technique for catalytically reacting under liquid phase conditions simultaneously in each a plurality of substantially identical reaction tubes a mixture of two at least partially immiscible liquids of differing density, the mixture in each tube being such that the liquids are substantially equally distributed herein in a substantially uniform prechosen weight ratio.

Other and further objects, purposes, advantages, aims, utilities, and features will be apparent to those skilled in the art from a reading of the present specification and drawings.

DETAILED DESCRIPTION

Figures 1, 2, 3, 4, 5, 6, 7:
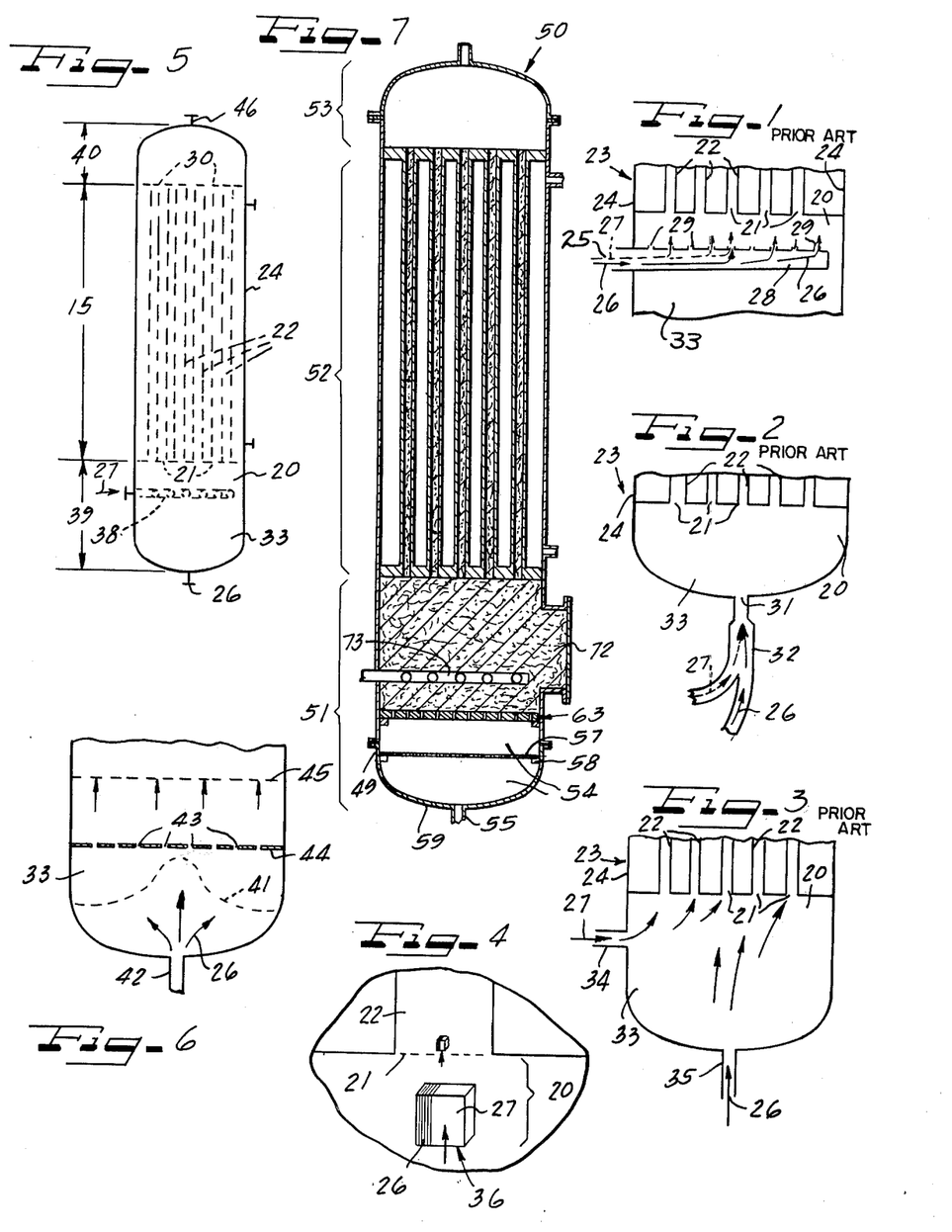
FIG. 1 diagramatically illustrates problems associated with the use of a prior art fluid intermixing technique for purposes of achieving equal distribution between two fluids of differing density being charged to a tubular reactor having a plurality of reaction tubes.
FIG. 2 is a view similar to FIG. 1 but showing a different form of prior art fluid mixing technique.
FIG. 3 is a view similar to FIG. 1 but showing another form of prior art fluid mixing technique.
FIG. 4 illustrates the problem of obtaining a constant weight ratio of one fluid relative to another per prechosen unit of mixed fluid volume transversely across the path of motion of such fluid mixture at the mouth of a single tube in a multi tube sequence.
FIG. 5 is a diagrammatic, simplified sectional type view illustrating one version of an apparatus of the present invention.
FIG. 6 diagrammatically illustrates an improved and preferred version of a feed distribution zone for the system of FIG. 5.
FIG. 7 is a vertical, sectional view of an embodiment of the present invention incorporating the operative principles illustrated in FIGS. 5 and 6.
Figure 8:
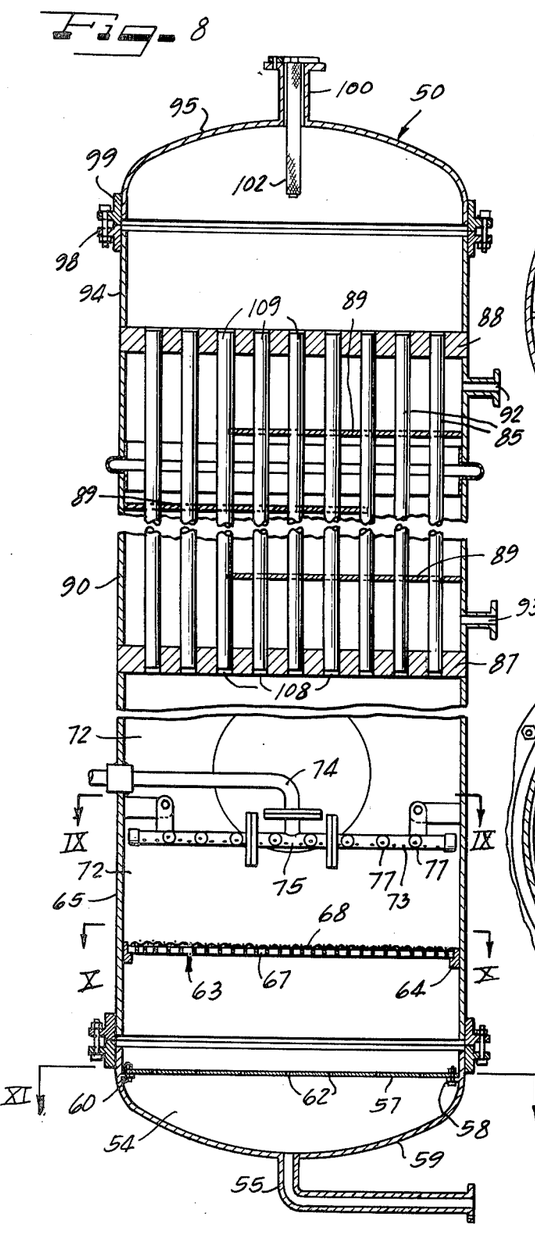
FIG. 8 is an enlarged, detailed vertical sectional view through the device of FIG. 7, some parts thereof broken away, and some parts thereof shown in section, this view being taken at right angles to the view illustrated in FIG. 7.

The difficulties of achieving a substantially equal distribution of two liquids of differing density over a predetermined zone, such as a zone 20 immediately preceding the entrances 21 of each of a plurality of tubes 22 in a tubular reactor 23, the tubes 22 being contained within a shell 24, are illustrated in FIGS. 1-3. Thus, in FIG. 1, a more dense liquid fluid 26 and a less dense fluid 27 are both charged into the mouth 25 of a tube 28 equipped with a plurality of longitudinally spaced (relative to tube 28) nozzles 29, the tube 28 extending transversely across zone 20. Even when the fluids 26 and 27 are charged at equal pressures and temperatures, the less dense fluid 26 tends to leave tube 28 through nozzles 29 before the more dense liquid 26; that is, the residence time of less dense fluid 27 is less than the residence time of more dense liquid 26 in tube 28. Thus, more dense liquid 26 tends to separate from less dense fluid 27, so that terminal nozzles 29 of tube 28 are richer in liquid 26 than fluid 27, and vice versa for initial nozzles 29. Hence, a tube distribution arrangement of FIG. 1 is unsatisfactory for solving the problems faced on this present invention.

In FIG. 3, a less dense fluid 27 is fed into chamber 33 through pipe 34 just below zone 20 and comes into contact with a more dense liquid fluid 26 upwardly flowing in chamber 33 from an input pipe 35. As the arrows in chamber 33 suggest, the fluids 26 and 27 tend to mix only to a limited or incomplete extent, since more of the less dense fluid 27 enters the entrances 21 of tubes 22 nearest pipe 34 than otherwise, and fluids 26 and 27 tend to pass through zone 20 without achieving a desired uniform distribution, so that individual tubes 22 contain differing compositions of fluids 26 and 27. Hence, this distribution arrangement of FIG. 3 is unsatisfactory for solving the problems faced in this present invention.

What is required in a distribution system for achieving equal distribution of such fluids 26 and 27 (as respects intermixing and flow characteristics) to each of the plurality of tubes 22 in accord with the present invention is the establishment, in a zone 20 in a bottom chamber 33, of a uniform, mixed dispersion of fluid 27 in liquid fluid 26 flowing preferably upwardly in a manner such that the overall velocity profile across any transverse section of zone 20 in bottom chamber 22 is substantially flat and uniform (see FIGS. 1-3). The mixing should be sufficient to produce a composition which, in any unit volume 36 thereof, as shown in FIG. 4 across a transverse section of zone 20 in chamber 33 immediately below tube entrances 21, is substantially the same. It is sufficient for the size of a unit volume 36 to be about the same as that across the tube entrances 21, although the size of such a unit volume can be substantially smaller, because it is not necessary to achieve a higher degree of mixing to obtain uniform distribution to tubes 22 for purposes of the present invention.

The above indicated limitations and problems of prior art techniques have been overcome, and the desired substantially equal distribution achieved in the present invention, (see FIG. 5), by having the more dense liquid or fluid 26 enter a chamber 33 which contains a bed of an inert, solid, particulate material (not shown in FIG. 5). The liquid 26 fills the interstices in the bed of chamber 33 and flows preferably upwardly therein in a plug flow manner. Positioned generally transversely across chamber 33 below zone 20 is an injection means or conduit distribution network of some type, herein designated in its entirety by the numeral 38. The less dense liquid or fluid 27 is charged into network 38 and permitted to escape therefrom uniformly from a plurality of orifices generally evenly distributed transversely across the chamber 33. When liquid or fluid 26 meets liquid or fluid 27, a substantially equal distribution of liquid or fluid 27 in liquid or fluid 26 results, so that a desired substantially equal distribution of liquid or fluid 26 relative to liquid or fluid 27 takes place in a feed distributor 39 before such resulting mixture of liquids or fluids 26 and 27 enter the entrances 21 of tubes 22 of reactor 15.

The tubes 22 may, and usually preferably are, substantially similar to one another and are packed with a fixed catalyst bed (not shown in FIG. 5), the catalyst being supported in the tubes 22 by the inert, particulate material in chamber 33. In operation, a fluid circulated between shell 24 and tubes 22 is used to remove or supply heat to reactor 15 depending on whether the particular reaction is exothermic or endothermic. A product collection and discharge chamber 40 is provided at terminal ends 30 of tubes 22, chamber 40 having an exit port 46.

Although the system of FIG. 5 is generally satisfactory, those skilled in the art will understand that, when the more dense liquid has a relatively low velocity in chamber 33, a non-uniform velocity profile may exist across a transverse section or chamber 33, particularly when there is used a single pipe 26 input, which is an undesirable effect from the standpoint of achieving a desired equal distribution of fluids 26 and 27 in tubes 22. To overcome this effect, an arrangement such as shown in FIG. 6 may be, and preferably is, employed. Here a distributor grid means or distributor 44 is transversely positioned across chamber 33. The particular grid means 44 in FIG. 6 is a plate equipped with equally sized holes or orifices 43 which are equally spaced thereacross in a regular pattern. The number and size of holes 43 are chosen so as to cause a resistance to flow of liquid 26 through holes 43. The result is that substantially the same flow of liquid 26 passes through each individual orifice 43. The non-uniform velocity profile represented by dotted line curve 41 below distributor 44 is thus reduced to a substantially flat, uniform velocity profile as represented by dotted line curve 45 above distributor 44, which is desirable for equal distribution of liquid 26 relative to liquid 27, in accord with the present invention.

The principles and features of FIGS. 5 and 6 are shown combined into the embodiment shown, for example, in FIGS. 7 through 13. Referring to these, there is seen an embodiment of the present invention which is herein designated in its entirety by the numeral 50. The assembly 50 is seen to comprise a feed distribution zone 51, a shell and tube isothermal reaction zone 52 suitable for a hydration or the like, and a product collection and discharge zone 53, the embodiment 50 is preferably used in an upright position with an up flow of reactants, the feed distribution zone 51 being below the reaction zone 52 and the product zone 53 being over the reaction zone 52.

A more dense liquid (not shown) is fed into a bottom cavity 54 of the feed distribution zone 51 through a pipe 55. There is no particular critical relationship between the size of pipe 55 and the cross sectional area of bottom cavity 54. Pipe 55 should be of sufficient size so as not to cause an excessive pressure drop into the system.

Transversely mounted across the interior of the bottom cavity 54 is an orifice plate 57. An inwardly projecting flange or ring 58 is mounted by welding or the like just above a preferably dished bottom portion 59 to the cylindrical wall portion 49 of cavity 54. Flange 58 supports the orifice plate 57, the orifice plate 57 here being secured to the flange 58 by a plurality of nut and bolt assemblies 60 extending through aligned holes in the respective orifice plate and flange 58. The orifice plate 57 is provided with a plurality of apertures 62 (see FIG. 11), the apertures 62 being preferably distributed regularly and uniformly across the plate 57.

There is no particular critical interrelationship in the spacing between the orifice plate 57 and the pipe 55, and, furthermore, there is no particular critical interrelationship between the apertures 62 and the diameter of pipe 55, so long as the desired pressure drop and creation of a uniform velocity profile across orifice plate 57 is achieved. Preferably, plate 57 is provided with apertures 62 which are equally sized and uniformly spaced. The size of the apertures 62 is selected to give a sufficient pressure drop across the orifice plate 57 to provide an essentially equal flow of liquid through each aperture 62 so that the result is an essentially flat velocity profile in the liquid phase of the liquid verticall moving upwardly above the plate 57 uniformly taken across the diameter of the distribution zone 51 above the orifice plate 57 in embodiment 50.

In general, all structural components coming into contact with the process fluids of the embodiment 50 are preferably formed of metal, preferably stainless steel.

Transversely extending across the top of the bottom cavity 54 is a catalyst bed support grid assembly 63. The grid assembly 63 is supported by a ring support 64 secured to cylindrical wall portion 65. Ring 64 is flanged on its inner wall and adapted to receive and support the grid assembly 63. The outer wall of the ring support 64 is secured as by welding or the like to the cylindrical side wall 65 of embodiment 50. Although nut and bolt assemblies (not shown) may be used to secure the grid assembly 63 to the ring support 64, such are obviously not necessary. Any convenient support means for a grid assembly may be employed.

In the embodiment shown, the grid assembly 63 is seen to comprise a grating 67 over the upper face of which is extended a wire mesh cloth 68. The grating 67 can be of any convenient construction; for example, it can comprise a plurality of long bars 69 in spaced parallel relationship to each other having welded therebetween a plurality of cross bars 70, there being open areas thus defined between the long bars 69 and the cross bars 70. The wire mesh cloth 68 can be of any conventional type.

In general, it is preferred that the combination of grating 67 with wire mesh cloth 68 be such that the combination presents a generally uniform configuration transversely extending across the cavity 54. Preferably, in addition, the assembly of grating 67 and cloth 68 should be uniform in the sense that it provides no restriction to flow of fluid or liquid therethrough. Furthermore, the grating 67 should be sufficiently strong to support the inert particle fill and the catalyst, all as herein described, and the wire mesh cloth 68 should have apertures between adjacent wire mesh members thereof to permit retention on the cloth 68 of substantially all of particulate material within a given bottom cavity 54. In general, the primary function of the grid assembly 63 is to support the solid particulate material thereabove.

Above the grid assembly 63, and extending to the top of the feed distribution zone 51 within the cylindrical side wall 65, is a cavity 72 which is filled with a solid, particulate, inert material (not shown). Any convenient such material may be used. Such particulate material should have sufficient strength to support the catalyst in the tubes, if such is present, and such should be inert to the process fluids. Also, it should preferably be non-porous as respects individual particles (as distinct from the bed itself). Packing in a bed should be preferably random so flow maldistribution is not induced. Thus, the inert material can, for example, be conventional tower packings fabricated from shapes of stainless steel or ceramic such as Intalox R saddles (a trademark of the Norton Co.,), or PALL R rings (a trademark of the Norton Co.,) or the like. Also, the inert, particulate material can be, for example, essentially spherical or cylindrical pellets made from fused alumina, or the like. In general, the size of the solid particulate inert material is a function of a particular unit volume of equal distribution desired for a mixture of more dense liquid in a less dense liquid. The relationship between the individual particles depends upon the degree to which they are compacted in the feed distribution zone 51, and similar factors. In general, the size of the particles comprising the inert material fill should be preferably smaller in average diameter than the cross sectional area or cross sectional diameter of the mouth of the individual tubes comprising the tubular reaction zone. The minimum average particle size is preferably greater than the average aperture size in the wire screen cloth 68 described above. In general, a suitable average particle size range is from about 0.2 inch up to about 2.6 inch within the limitations above indicated. Such a minimum size provides a minimum of interference in flow characteristics of liquids or fluids passing therethrough as desired in accordance with the preferred practice of the present invention.

Within the cavity 72 is positioned a distributor assembly 73. The assembly 73 transversely extends across the feed distribution zone 51 and is adapted to provide a means for inputing into the feed distribution zone 51 a low density liquid. In the embodiment shown, the distributor assembly 73 is preferably in the form of a ladder configuration. A feed pipe 74 conveys a low density liquid through the wall 65 to a central region of the assembly 73 where the feed pipe 74 interconnects with a primary distributor conduit 75. Interconnected with the primary distributor conduit 75 and laterally extending outwardly therefrom in opposed, transversely aligned relationship are pairs of secondary distribution conduits 77. The individual secondary distribution conduits 77 are generally in spaced, parallel relationship to one another.

As a constructional aid, and to facilitate mounting and demounting a distributor assembly 73 in feed distribution zone 51, the feed pipe 74 is provided with a joint 78 (see FIGS. 13 and 14) in a region thereof adjacent the primary distributor conduit 75. The joint 78 is conveniently formed by a pair of flanges 79 and 80, one flange 79 being secured to an adjoining end portion of each section of pipe 74 on either side of joint 78. The flanges 79, with appropriate gasketing material (not shown) therebetween, are conveniently clamped together by means of nut and bolt assemblies 82. The primary distribution conduit is equipped with joints 83 and 84, each joint 83 and 84 being similarly constructed to the manner of joint 78.

The primary distribution conduit 75 on its downwardly facing cylindrical wall portions is equipped with a plurality of orifices 83. Similarly, the secondary distribution conduit on its downwardly facing cylindrical wall portions is equipped with a plurality of orifices 84. In the embodiment shown, the orifices 83 are arranged in circumferentially spaced pairs at axially spaced intervals along the primary distributor conduit 75, and similarly for the orifices 84 of the secondary distributor conduits 77. The angular relationship between circumferentially spaced pairs can be as desired, although in the embodiment shown the orifices 83 are disposed at an angle relative to each other of about 25° while the orifices 84 are disposed at an angle relative to each other of about 30°.

In general, the orifices in the distributor can face in any direction desired, upwards, downwards or sidewards. However, a downwardly opening orifice orientation is generally preferred. Any convenient, operable distributor mechanism known to the art may be employed in the practice of this invention, as those skilled in the art will appreciate, for the less dense and the more dense liquids. (see for example, Perry and Chilton fifth edition "Chemical Engineers Handbook", Section 5, pages 47 and 48 (1973)).

Adjacent the feed distribution zone 51 is a shell and tube isothermal reaction zone 52. Zone 52 contains a plurality of tubular members 85 in spaced relationship to each other, preferably in transversely equally spaced, longitudinally parallel relationship. A bottom tube sheet 87 and a top tube sheet 88 each has appropriate bores therein adapted for mounting and positioning the respective individual tubes 85, the respective tubes 85 being conveniently welded to the tube sheets 87 and 88 in the manner conventionally known to the art of shell and tube heat exchanger and reactor construction in the chemical industry. A plurality of baffle plates 89 are preferably transversely positioned in patterned transverse, longitudinally spaced fashion across the individual tubes 85 within a shell 90 which extends about the entire assembly of tubes 85 and baffle plates 89. A heat exchange fluid is circulatable within the shell 90 in and around the outside walls of the tubes 85 through the heat exchange fluid input ports 92 and 93. The tubes 85 may be one preferably packed with a particulate, solid catalyst bed (not shown) when using embodiment 50, as those skilled in the art will appreciate. When the tubes 85 are so packed the particulate solid material packed in cavity 72 serves to support and hold the catalyst in the tubes 85. The catalyst bed support grid assembly 63 supports both the catalyst material in the tubes 85 as well as the particulate material in cavity 72.

A mixture of less dense and more dense liquid produced in the feed distribution zone 51 passes into the tubes 85 of zone 52 wherein a desired reaction occurs. If the reaction in zone 52 is exothermic, heat is removed by means of coolant fluid circulated within the shell 90. If the reaction is endothermic, heat is supplied through a heat exchange medium circulated within the shell 90. After passing through the tubes 85, a reaction product enters product collection and dischage zone 53 which is formed by a cylindrical wall or body portion 94 and a dome or head portion 95 integrally interconnected, the body portion 94 and the head portion 95 being secured to one another with nut and bolt assemblies through the medium of a conventional clamp 97 secured to the edges of each of a pair of flanges 98 and 99, flange 98 being secured to the upper end of the cylindrical portion 94; flange 99 being secured to the lower end of the dome portion 95. Appropriate gasketing material (not shown) may be inserted between the flanges 98 and 99 of the cylindrical portion 94 and the dome portion 95.

Head portion 95 is equipped with a flange exit pipe 100 from which a reaction liquid in the zone 53 exits. In the embodiment shown the pipe 100 is fitted with a wire mesh cloth 102 having an open area of from about 24 to 30% as a means of separating any solid particulate material carried upwardly from the interior of the tubes 85 into the zone 53. Use of a screen 102 constitutes an optional but preferred element in an embodiment 50.

The screen 102 is an optional, but preferred feature, of the embodiment 50, and comes into practical use in the event of a possible process upset in which catalyst within the tubes 85 is carried upwardly into the chamber 9. Embodiment 50 is preferably equipped with a manway 103 having a removable cover 104, cover 104 comprising a plate pivotally mounted against a flanged rim 105 on manway 103 by means of nut and bolt assemblies 107. Manway 103 provides a convenient entry port for cleanout and maintenance of an embodiment 50, as those skilled in the art will appreciate.

In one mode of operation of an assembled and functional embodiment 50, the embodiment 50 is mounted in a vertical position, and a more dense liquid is pumped into pipe 55 and enters the feed distribution zone 51. When the liquid level rises to plate 57, the liquid passes through the apertures 62 therein, and continues to rise upwardly into the bed of particulate material in zone 72 through the catalyst bed support grid assembly 63. Into zone 72 through the feed pipe 74 is charged a less dense liquid which is distributed by the distribution assembly 73 transversely across the zone 72 into the particulate material therein. The more dense liquid flows around the outside of the distribution assembly 73 and is essentially unimpeded thereby. The less dense liquid flows inside of the distributor assembly 73 and leaves it via the orifices 83 and 84 which are equally spaced along the elements of the distributor assembly 73. As with the case of the apertures 62 in orifice plate 57, The orifices 83 and 84 are sized for a pressure drop which results in approximately equal flow of less dense liquid through each aperture 83 and 84.

This arrangement results in a substantially uniform distribution of the less dense liquid droplets in the more dense liquid continuous phase. When such mixture of less dense with more dense liquid reaches the top of the distribution zone 51, the liquid mixture is flowing with a substantially flat viscosity profile in such region (taken transversely across the top of the distribution zone 51). The inlet or entrance 108 of each tube 85 is consequently exposed to a reactant feed mixture of approximately uniform composition, as desired.

In accordance with the teachings of the present invention, the injection of more dense liquid and less dense liquid through separate distribution networks into a bed of particulate material has the advantage of positively distributing each respective such liquid across a predetermined diameter of exposed mouths of tube portions of a shell and tube isothermal reaction zone 52. While the respective two phases of immiscible less dense and more dense liquid may be thoroughly mixed externally before entering to the zone 51, it is exceedingly difficult to prevent the respective phases from separating and flowing non uniformly through the feed distribution zone 51 if such are fed in together. This is because of the density differential between less dense liquid and more dense liquid which, as indicated earlier in relation to FIGS. 1-3 causes the less dense liquid phase to tend to rise more rapidly than the more dense phase so that the less dense phase tends to channel straight upwardly from any single injection point.

Figure 14:
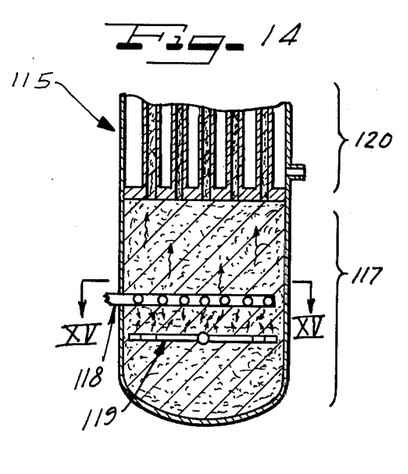
FIG. 14 illustrates a fragmentary vertical sectional view of an alternative embodiment of the present invention showing a feed distribution system adapted for use in the present invention in a partially schematic form for illustration purposes.
Figure 15:
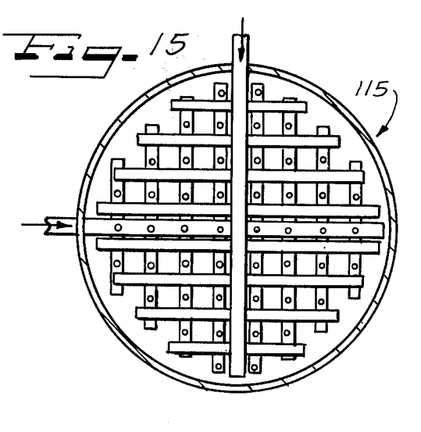
FIG. 15 is a transverse sectional view taken along the line XV—XV of FIG. 14.

In practice the process of the present invention can be carried out with the zones 51, 52 and 53 in any convenient orientation. The embodiment 50 is intended for utilization in a vertical configuration. In FIGS. 14 and 15 is illustrated an alternative embodiment 115 of apparatus similar to embodiment 50. In embodiment 115, a feed distribution zone 117 at the bottom of embodiment 115 is filled completely (as shown by shade lines) with a particulate material (not shown) having a form and composition similar to that employed in the embodiment 50. Embodiment 115 employs a pair of vertically spaced ladder distribution assemblies 118 and 119. Each such assembly 118 and 119 is similarly constructed to the distributor assembly 73 and functions similarly. Construction of the embodiment 115 is similar to that of embodiment 50 as respects the shell and tube isothermal reaction zone 120 thereof, as well as for the product collection and discharge zone (not shown in FIGS. 14 and 15).

The embodiment 50 is preferred over the embodiment 115 because in embodiment 115 a dead space inherently exists below distributors 118 and 119. The existance of such a dead space may result in a long residence time for some fraction of the feed mixture in the space below distributors 118 and 119 in embodiment 115. Such a long holdup may make it difficult to flush out embodiment 115, as when shutting it down. Such a long holdup may also result in undesirable side reactions if high temperatures are employed.

Figure 16:
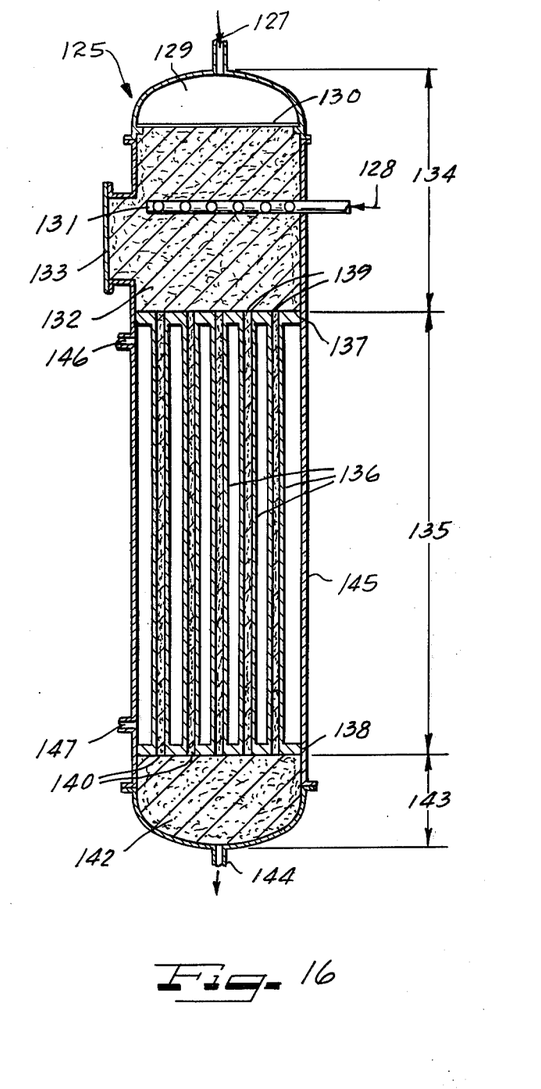
FIG. 16 is a vertical sectional diagrammatic view of a further embodiment of an apparatus of the present invention.

In FIG. 16 is shown another embodiment of an apparatus of the present invention, herein designated in its entirety by the numeral 125. Embodiment 125 employs a less dense liquid or fluid inlet 127 and a more dense liquid or fluid inlet 128. A less dense fluid (not shown) charged through inlet 127 passes into a chamber 129 and out through a perforated distributor, here shown as a plate 130, which serves to produce a cross-sectionally uniform velocity profile in downwardly moving fluid in embodiment 125. As fluid from plate 130 moves forwardly (downwardly), it passes around a ladder distributor network fluid injector 131 from which a more dense liquid (not shown) issues, injector 131 being charged with such fluid through fluid inlet 128. Below injector 131 is a bed 132 of solid, inert, particulate material (not shown). Access to bed 132 for maintenance purposes is conveniently had by means of a manway 133. The entire region from the inlet 127 to the bottom (or forward) end of bed 132 can be considered a feed distribution zone 134.

Below the feed distribution zone 134 is a reaction zone 135 which has a plurality of tubes 136 held in spaced relationship relative to each other by means of tube sheets 137 and 138. Liquid or fluid (not shown) from the bottom of bed 132 enters the entrance ends 139 of tubes 136, passes through tubes 136, out the exit ends 140 of tubes 136, and into a collection chamber 142, chamber 142 being considered as a collection zone 143 in embodiment 125. An exit port 144 provides a product removal means for zone 143 and chamber 142. A heat exchange fluid is circulatable around the outside walls of tubes 136 in a shell 145 equipped with parts 146 and 147.

The tubes 136 may be and preferably are filled with a fixed bed particulate catalyst (not shown). When a catalyst is used, chamber 142 is filled with an inert particulate material (not shown) which may be the same as that in bed 132. If the tubes 136 are not so filled with catalyst, a screen or the like (not shown) may be transversely extended across the plate 137 at the bottom of bed 132 to hold bed 132 particulate material in place.

In general, construction of embodiment 125 is similar to that of embodiment 50 (above), as those skilled in the art will appreciate.

As can be seen from the foregoing description, the present invention involves a preferred process which may be practiced with an embodiment 50 or 115, wherein two at least partially immiscible liquids of different density are reacted together under conditions of substantially equal distribution. The process involves the charging of the more dense one of the two partially immiscible liquids to a lower portion of a feed distribution zone. Such charging is conducted in a manner such that a substantially uniform velocity profile is produced transversely across the feed distribution zone. This zone is conveniently and preferably substantially completely filled with a solid particulate inert material having a porosity at least sufficient to permit the more dense liquids to flow therethrough.

Concurrently, one charges to an upper portion of the feed distribution zone in a region thereof extending generally transversly thereacross the less dense of the two liquids. The charging is accomplished using a plurality of orifices each of which has a very small cross-sectional area relative to the cross-sectional area of the zone at the transverse position within such zone that such charging takes place.

Typically the orifices in a feed injection means preferably fall in the diameter range of from about 0.2 to 0.07 inch, though larger or smaller sizes can be used. Larger diameters appear presently to encourage poor mixing characteristics while smaller diameters are perhaps more prone to plugging. The orifices are preferably generally uniformly distributed with preferebly equal sizes across a region in the distribution zone. Flow through the orifices of a less dense liquid or a more dense fluid, as the case may be, depends upon form of a given distributor zone and operating conditions but preferably is substantially the same for all orifices.

The resulting mixture of the less dense and the more dense liquids in a distribution zone is caused to flow through the feed distribution zone above the region of the fluid injection for a distance (preferably vertical) which is at least sufficient to substantially uniformly distribute the less dense fluid as a discontinuous phase within the more dense fluid transversely across the top end portion of the feed distribution zone.

After the feed distribution zone the resulting mixture of such liquids is moved substantially immediately as well as simultaneously into the entrance of each one of a plurality of tubular reaction zones. Such tube entrances are positioned in a region generally transversely extending across the top of the feed distribution zone. By this technique the mixture from the feed distribution zone enters each tubular reaction zone simultaneously.

Next, the mixture in the tubular reaction zones is subjected to predetermined liquid phase conditions of temperature, catalysis and time. Thereafter, the resulting so reacted mixture exits from the ends of the tubular reaction zones and is collected in a common chamber. Finally, the so reacted mixture or product is removed from the chamber.

In such a preferred process of this invention, one preferred more dense liquid is water, while the less dense liquid is preferably an organic liquid having a molecular weight ranging from about 28 to 200. One much preferred organic liquid is a nitrile, such as an alkenyl nitrile, and a most preferred alkenyl nitrile is acrylonitrile. Another much preferred organic liquid is an olefin, especially propylene. Those skilled in the art will appreciate that any one of a variety of liquid pairs which are more dense or less dense relative to each other may be employed using apparatus and method as taught in this invention.

In one preferred mode of practicing the method of the present invention, the more dense liquid is so mixed with the less dense liquid that the ratio by weight of more less dense liquid to less dense liquid ranges from about 9:1 to 1:3 over a unit mixture volume ranging from about $(0:4)^3$ to $(2.6)^3$ in$^3$ although any convenient such weight ratio may be employed, depending upon the particular immiscible liquids involved, the degree of immiscibility of one liquid relative to the other, reaction zone tube size, etc.

Preferably, the techniques of the present invention are practiced using tubular reaction zones which have an average diameter ranging from about 0.4 to 2.6 inches, all tubes in one reaction zone having the same diameter.

Those skilled in the art will appreciate that any convenient or desired set of reaction conditions may be employed in the reaction zone to produce a desired product, within the teachings of this invention. For example, in the case of hydrolyzing acrylonitrile using a two-phased starting feed of acrylonitrile and water, the tubular reaction zones are each substantially isothermal, and are each maintained at a temperature in the range from about 100° to 300° F. The weight ratio of starting acrylonitrile to water in the feed intermixture is between about 0.3 and 3. The weight hourly space velocity is between about 0.1 and 10.0 hrs$^{-1}$. The process pressure is sufficient to maintain substantially liquid phase conditions in both said feed distribution zone and said tubular reaction zones. The catalyst particle size is between about 0.01 and 0.49 inches, and has an initial activity between 0.25 and 2.0. The catalyst is a copper catalyst, preferably Raney copper.

For another example, in the case of hydrating propylene using a two-phased starting feed of acrylonitrile and water, the tubular reaction zones are each substantially isothermal and are each maintained at a temperature in the range from about 100° to 300° F. The weight ratio of starting propylene to water in the feed intermixture is between about 0.1 and 1.0. The process pressure is sufficient to maintain a liquid phase in both said feed distribution zone and in said tubular reaction zone. Pressures can in the range from about 500 to 5000 PSIG. The weight hourly space velocity is between about 0.3 and 20. The catalyst particle size is between about 0.01 and 0.49 inches, and the catalyst is selected from the group consisting of at least one acidic ion exchange resin and tungsten oxide.

Other and further reaction processes and reaction process conditions will be readily apparent to those skilled in the art from a reading of the present invention taken with the drawings.

It is an inherent fact that, based upon the present state of the art, it is very difficult to quantitatively demonstrate directly the degree of intermixing achieved by the techniques of the present invention, particularly as respects events in a feed distribution zone and/or the uniformity of flow rates, and/or the constancy of rate is between more dense and less dense fluids. There is no intent to be bound by theory herein. The techniques of the present invention are believed to produce better results in terms of conversion characteristics in a product based on a starting material than anything in the relevant prior art.

Other and further embodiments and variations of the present invention will become apparent to those skilled in the art from a reading of the present specification taken together with the drawings and no undue limitations are to be inferred or implied from the present disclosure.

EMBODIMENTS

The present invention is further illustrated by reference to the following Examples. Those skilled in the art will appreciate that other and further embodiments are obvious and within the spirit and scope of this invention from the teachings of these present Examples taken with the accompanying specification and drawings.

EXAMPLE 1

This example illustrates a preferred technique for determining catalyst activity for a catalyst to be used in hydrolyzing acrylonitrile to acrylamide using a two phased starting feed of acrylonitrile and water.

A reactor is formed of a double pipe heat exchanger design. The inner tube, which constitutes the reaction zone, is a five foot length of 304 SS., schedule 10S pipe which has an inside diameter of 1.097 inch and an outside diameter of 1.185 inch. This pipe is vertically positioned and equipped to allow introducing the feed at the bottom and withdrawing product from the top. The inner tube is uniformly surrounded by a jacket which is provided with an inlet at the bottom of the jacket and an outlet at the top of the jacket to allow circulating an oil for removing the heat of reaction.

A thermowell of about ⅛ diameter is inserted from the top and runs the length of the inner pipe to allow temperature measurements to be made throughout the reaction zone.

When this reaction is used to determine activity of a catalyst, during operation of this reactor, acrylonitrile and water are separatedly pumped from volumetrically calibrated feed tanks, combined, heated, and introduced into the bottom of the reactor. The reactor is maintained under pressure as necessary to allow maintaining liquid phase conditions. Product leaving the reactor is cooled before reducing pressure to atmospheric. Product is collected in a final receiver.

The feed tanks are sparged with nitrogen for a brief time before the beginning of a run to minimize oxygen contained in the feeds to the reactor.

Samples of product are analyzed for weight % acrylamide, weight % acrylonitrile, and weight % water to determine conversion levels (100 weight percent total product weight basis).

The procedure to determine catalyst activity is as follows: A measured weight of catalyst is charged to a tubular reactor so as to occupy approximately 50 cubic inches and a series of tests are run as previously described. The tests are run at different contact times with all other variables held constant, as follows:

1. Arithmetic mean catalyst bed temperature of 210° F.
2. Feed composition 100 weight % basis of 35 weight % acrylonitrile and 65 weight % water.

Contact time is inversely measured as weight hourly space velocity (WHSV), which is defined as weight hourly feed rate divided by catalyst weight in the reaction zone.

The contact times are varied to bracket an 80% conversion level. The WHSV required for 80% conversion (WHSV$_{80}$) is estimated by graphical or statistical interpolation. The catalyst activity (a) is then calculated from the following expression:

$$a = 0.6 \, (WHSV_{80})$$

All catalyst activity values in this application are measured by the procedure described in this Example.

WHSV's in the range of 0.4 to 6.0 are useful starting points to bracket the space velocity required for 80% conversion (WHSV$_{80}$), the last being an abbreviation for weight hourly space velocity needed for 80% conversion.

EXAMPLE 2

This example demonstrates the production of a catalyst suitable for hydration of acrylonitrile, to acrylamide using a two phased mixture of acrylonitrile and water.

Small ingots of a 50% copper, 50% aluminum alloy are crushed using a roll crusher and screened to obtain a 6 to 8 mesh particle size cut from the crushings. These 6 to 8 mesh alloy particles are then activated with caustic to form a granular Raney copper catalyst by the following procedure:

A reaction vessel of approximately 30 ga. which is equipped with a cooling jacket and an agitator is charged with about 6.5 lbs of the 6 to 8 mesh alloy particles, 67 lbs. of deionized water, and about 0.08 lbs. of dissolved gluconic acid and the vessel is maintained at about 86° F. Caustic in the form of an aqueous solution of 50 wt. % Na OH is then added to the mixture in the vessel continuously with stirring over a 5 hour period so that a total of 26.5 lbs. of 50% caustic is thus added to the vessel at the temperature indicated. After such caustic addition is completed, the vessel is maintained with stirring for an additional 5 hours. During the entire period of activation the temperature of the liquid in the vessel is maintained by adjusting the rate of coolant to the vessel jacket.

The product Raney copper granules thus produced are washed until wash water shows a neutral pH. These product washed granules are screened to remove fines smaller than 20 mesh and then stored under deionized water.

When evaluated for catalytic hydrolysis activity in the manner described in Example 1, this material is found to have an activity of about 1.0.

EXAMPLE 3

This example illustrates the hydrolysis of a two phased starting feed of acrylonitrile and water using the technology of Examples 1 and 2 and the embodiment 50 herein described (see FIGS. 7-13 and accompanying description).

Figure 9:
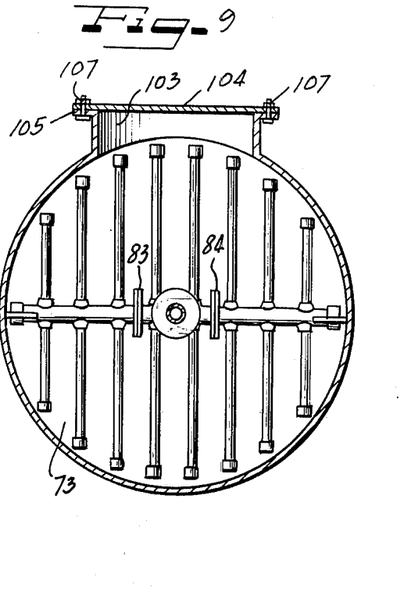
FIG. 9 is a transverse sectional view taken along the line IX—IX of FIG. 8.
Figure 10:
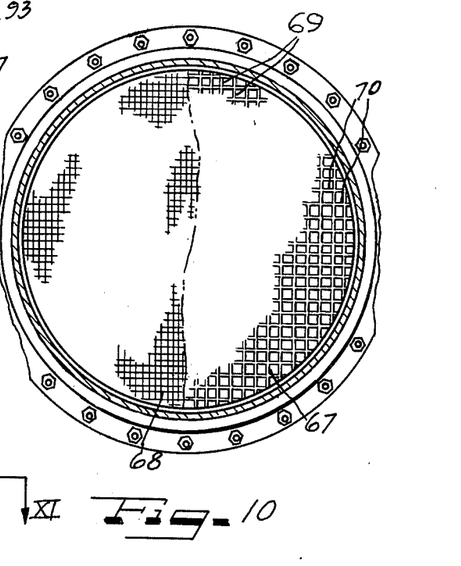
FIG. 10 is a transverse sectional view taken along the line X—X of FIG. 8.
Figures 11, 12, 13:
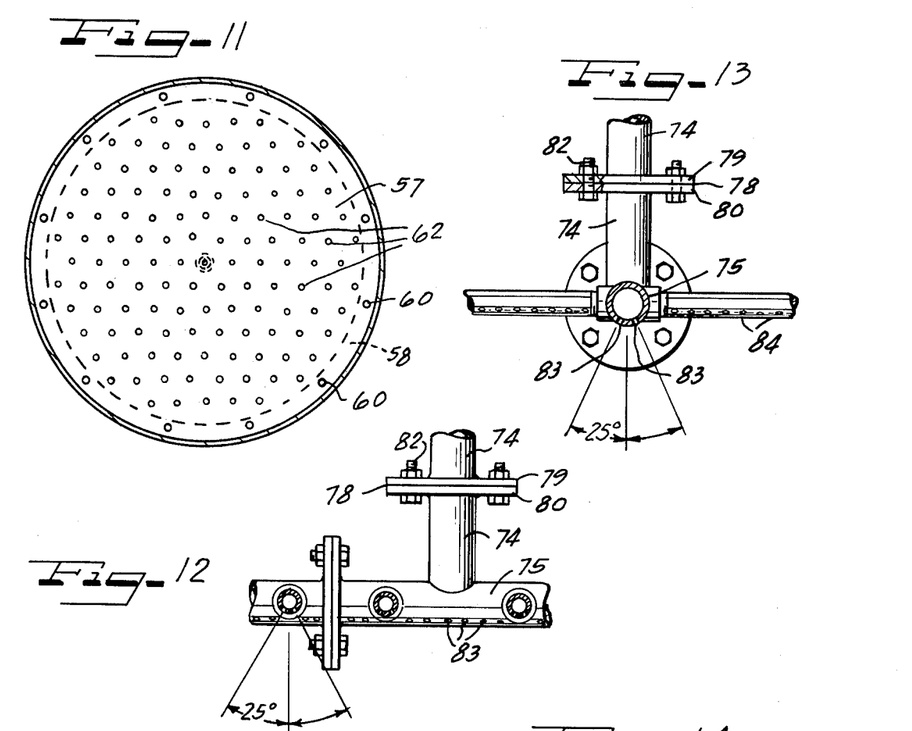
FIG. 11 is a transverse sectional view taken along the line XI—XI of FIG. 8.
FIG. 12 is a fragmentary vertical sectional view through the ladder distribution element illustrated in FIGS. 8 and 9.
FIG. 13 is a view similar to FIG. 12 but taken at a direction normally with respect thereto.

The reactor contains 224 tubes which are 8 feet long and 1½ inches outside diameter. The tubes are mounted parallel inisde a 32 inch inside diameter shell on a 1⅞ inch triangular pitch relative to each other. The bottom distribution chamber is 32 inches inside diameter and approximately 4.5 feet long. The top product discharge chamber is 32 inches in diameter and approximately 12 inches long. The water distributor plate is equipped with approximately 110 holes which are each 3/16 inch in diameter and which spaced from each other on a 2½ inch triangular pitch. The acrylonitrile (less dense liquid) distributor has 12 arms as shown in FIG. 9 and is equipped with approximately 230 holes which are each 1/16 inch in diameter and uniformly spaced on the secondary and primary manifolds. The support plate is a square grid grating covered with a wire cloth.

The cavity between the support grid and the lower tube openings is filled with substantially spherical balls of fused alumina which are approximately 0.5 inches in diameter.

The tubes are filled with a 6 to 10 mesh granular Raney copper catalyst similar to that described in Example 2 which has an initial activity of approximately 1.0 determined as described in Example 1.

The reactor is equipped with a cooler and a circulation pump which are interconnected in a manner which allows circulating water through the reactor shell at predetermined substantially constant temperature. Controls are provided to allow closely controlling circulating water temperature.

Water at about 170° and acrylonitrile at room temperature are each fed to their respective distributors at temperatures of about 170° F using rates which give a WHSV (total weight hourly feed rate divided by catalyst weight) of 3.0 and an overall feed composition of 35 weight % acrylonitrile and 65 weight 1/0 water. The system is maintained at 100 PSIG pressure. The circulating water temperature is adjusted to give an average bed temperature of 170° F.

The product effluent from the reactor after steady state conditions are reached is analyzed by gas chromatography for weight % acrylamide and wt. % water (100 wt. % total basis). Conversion of acrylonitrile to acrylamide is approximately 28% (based on starting acrylonitrile). Impurities are less than 0.1 weight %. The conversion levels obtained in the practice of this Example are substantially the same within the limits of experimental accuracy as the conversion levels obtained in the single tube reactor of Example 1 operated at substantially the same reaction conditions of temperature, acrylonitrile to water ratio, pressures, and weight hourly space velocity. Consequently, the liquid distribution to the different tubular reaction zones in the reactor of this example is sufficiently uniform as respects distribution and flow characteristics to produce optimal conversion results in the given catalyst bed volume of the apparatus used in this Example.

EXAMPLE 4

This example illustrates the hydrolysis of a two phased starting feed of propylene and water using the embodiment 125 hereinabove described. (see FIG. 16 and accompanying description).

The tubular reaction zones are each filled with a strongly acidic sulfonated polystyrene divinyl benzene ion exchange resin sold by Dow Chemical Company under the trade name Dower R 50WX8. The resin has a standard 20 to 50 mesh particle size range. The common exit chamber under the tubular reaction zones is filled with inert, nominally spherical alumina particles of approximately 0.5 inches in diameter which serve as support for the catalyst. The feed distribution zone above the tubular reaction zones is also filled with alumina particles of the same properties.

To insure that the ion exchange resin is in the acid form, a large excess of a 5% aqueous solution of $H_2SO_4$ is passed over the resin by pumping the acid solution into the upper light phase distributor and withdrawing the resulting solution from the product outlet. Deionized water is subsequently passed over the resin the same manner to wash excess acid out of the resin bed.

Liquid propylene is pumped to 1000 PSIG, preheated to 300° F, and pumped into the input port associated with the upper, light fluid, orifice plate distributor. Water is similarly pumped to 1000 PSIG, preheated to 300° F, and pumped into the input port associated with the lower, heavy fluid, orifice ladder distributor. Under the above conditions, the water forms a liquid phase and the propylene forms a highly dense gas phase, since the temperature is above the critical temperature (198° F) of propylene, and the total pressure is well above the vapor pressure of water at 300° F (67 PSIA).

Water and propylene are pumped at rates which result in a 10 to 1 mole ratio of water to propylene and a LHSV of about 1.0 LHSV is defined as liquid hourly feed rate (measured as liquid propylene and water at 70° F) divided by catalyst volume.

The tubular reaction zones are maintained at substantially isothermal conditions at an approximate reaction temperature of 300° F. The reaction zone is maintained at a pressure of 1000 PSIG.

Product leaving the output port is cooled and flashed through a valve to atmospheric pressure. Most unreacted propylene is vented as a gas, and a liquid product is collected. Analysis by gas chromatography of the liquid product demonstrates a substantial quantity of isopropanol is present in the product.

What is claimed is:

1. A process for mixing and reacting two at least partially immiscible fluids of differing density, one of which is substantially always in a liquid phase, under conditions of substantially equal distribution of said liquids comprising the steps of simultaneously and continuously, but in a sequential manner
   A. charging the more dense fluid to a first portion of a feed distribution zone, said first portion being located remotely relative to substantially all of the respective end entrance openings of each of a plurality of tubular reaction zones, in a manner such that a substantially uniform velocity profile of each of said plurality of tubular reaction zones in a common chamber, and
   G. removing said resulting so collected mixture from said chamber.

2. The process of claim 1 wherein said flowing is in a vertical direction.

3. The process of claim 2 wherein said flowing is upwardly.

4. The process of claim 2 wherein said flowing is downwardly.

5. The process of claim 1 wherein said more dense liquid is water.

6. The process of claim 1 wherein said less dense liquid is an organic liquid having a molecular weight ranging from about 28 to 200.

7. The process of claim 2 wherein said organic liquid is nitrile.

8. The process of claim 4 wherein said nitrile is an alkenyl nitrile.

9. The process of claim 5 wherein said alkenyl nitrile is acrylonitrile.

10. The process of claim 1 wherein said more dense liquid and said less dense liquid are so mixed in a weight ratio of more dense liquid to less dense liquid of from about 9:1 to 1:3.

11. The process of claim 2 wherein said tubular reaction zones each have an average diameter ranging from about 0.4 to 2.6 inches.

12. In a process for reacting two at least partially immiscible fluids of differing density, one of which is substantially always in a liquid phase, under conditions of substantially equal distribution of said liquids using a plurality of tubular reaction zones wherein a process flow stream comprised of said fluids is subjected to predetermined conditions of temperature, catalysis, pressure and time, the improvements which comprises the steps of simultaneously and continuously, but in a sequential manner:
   A. charging the more dense fluid to a first portion of a feed distribution zone, said first portion being located remotely relative to the respective end entrance openings of each of said tubular reaction zones, in a manner such that a substantially uniform velocity profile of said more dense fluid is produced transversely across said zone relative to the direction of fluid flow in said feed distribution zone, said feed distribution zone being substantially completely filled with a solid, particulate, inert material having a porosity at least sufficient to permit said more dense fluid to flow therethrough, B. charging the less dense fluid to a second portion of said feed distribution zone, said second portion being located between said first portion and said reaction zone, in a manner such that a substantially uniform velocity profile of said less dense fluid is produced transversely across said zone relative to the direction of fluid flow in said feed distribution zone, C. flowing the resulting mixture of said fluids through said feed distribution zone for a distance at least sufficient to completely and substantially uniformly intermix said respective fluids, D. moving the resulting such intermixture into substantially all of the respective end entrance openings of each of said tubular reaction zones, at a substantially equal flow rate to each of said tubular reaction zones, the weight ratio of such more dense liquid to such less dense liquid in said intermixture as such enters each of said end entrance openings being substantially the same.

13. The process of claim 9 wherein:

A. said tubular reaction zones are each substantially isothermal, and are each maintained at a temperature in the range from about 100° to 300° F., B. the weight ratio of starting acrylonitrile to water in the feed intermixture is between about 0.3 and 3, C. the weight hourly space velocity is between about 0.1 and 10.0 hrs $^{-1}$, D. the process pressure is sufficient to maintain substantially liquid phase conditions in both said feed distribution zone and said tubular reaction zones, E. the catalyst particle size is between about 0.01 and 0.49 inches, F. the catalyst has an initial activity between 0.25 and 2.0., G. the catalyst is a Raney copper catalyst.

* * * * *